United States Patent [19]

Malone

[11] Patent Number: 4,973,773

[45] Date of Patent: Nov. 27, 1990

[54] PRODUCTION OF TETRAFLUOROETHYLENE

[75] Inventor: Brian S. Malone, Bear, Del.

[73] Assignee: E. I. Du Pont de Nemours and Company, Wilmington, Del.

[21] Appl. No.: 326,723

[22] Filed: Mar. 21, 1989

Related U.S. Application Data

[63] Continuation-in-part of Ser. No. 277,633, Nov. 29, 1988, abandoned.

[51] Int. Cl.$^5$ .................... C07C 17/24; C07C 17/34; C07C 17/26
[52] U.S. Cl. .................... 570/155; 570/153; 570/159
[58] Field of Search ............ 570/155, 159, 153

[56] References Cited

U.S. PATENT DOCUMENTS

| | | | |
|---|---|---|---|
| 2,709,182 | 5/1955 | Farlow | 260/653 |
| 2,709,192 | 5/1955 | Farlow | 260/653 |
| 2,725,410 | 11/1955 | Farlow et al. | 260/653 |
| 2,980,739 | 4/1961 | Farlow | 260/653.3 |
| 2,981,761 | 4/1961 | Farlow | 260/653.3 |
| 3,009,966 | 11/1961 | Hauptschein et al. | 260/653.5 |
| 3,081,245 | 3/1963 | Farlow | 204/169 |
| 3,262,981 | 7/1966 | Fainberg et al. | 260/653.3 |
| 3,308,174 | 3/1967 | Edwards et al. | 260/653.5 |
| 3,459,818 | 8/1969 | Ukihashi et al. | 260/653.3 |
| 3,471,546 | 10/1969 | Bjornson | 260/465.7 |
| 4,849,554 | 7/1989 | Cresswell et al. | 570/179 |
| 4,898,645 | 2/1990 | Voigt et al. | 570/153 |

FOREIGN PATENT DOCUMENTS

| | | | |
|---|---|---|---|
| 723699 | 12/1965 | Canada | 570/159 |
| 287219 | 10/1988 | European Pat. Off. | |
| 1306081 | 2/1973 | United Kingdom | 570/155 |

*Primary Examiner*—J. E. Evans
*Attorney, Agent, or Firm*—William H. Hamby

[57] ABSTRACT

Preparation of high yields of tetrafluoroethylene by preferably contacting pentafluoroethane and/or trifluoromethane with hot gas, preferably argon ($\geq 2000°$ K.) followed by rapid cooling of the reaction mixture, in less than one second, i.e., 0.001 to 0.1 second, to a temperature $\geq 800°$ K.

9 Claims, No Drawings

PRODUCTION OF TETRAFLUOROETHYLENE

RELATED APPLICATION

This case is a continuation-in-part of my copending application U.S. Ser. No. 07/277,633, now abandoned.

BACKGROUND OF THE INVENTION

U.S. Pat. No. 3,081,245 discloses and claims a process for the preparation of tetrafluoroethylene which comprises feeding a saturated perfluorocarbon to a continuous electric arc, passing the emerging gaseous product through a carbon bed at a temperature of 2700° C. to 2000° C., and thereafter quenching the resulting gaseous reaction product to a temperature below 500° C. in less than one second.

This process is limited to saturated perfluorocarbons such as tetrafluoromethane and hexafluoroethane.

U.S. Pat. No. 3,471,546 discloses and claims a process for the pyrolysis of fluoroform by contacting the same in a nitrogen plasma jet at a temperature in the approximate range 1000° to 2000° F. for a contact time of 0.0001 to 10 seconds producing a reaction effluent containing trifluoroacetonitrile, tetrafluoromethane, hexafluoroethane, tetrafluoroethene, and hexafluoropropene.

In the Example of the above patent the yield of tetrafluoroethylene is only 12.4 mole %. In the process of the instant invention a typical yield of tetrafluoroethylene is >60%.

SUMMARY OF THE INVENTION

A process for the preparation of tetrafluoroethylene by contacting a gas selected from Ar, HF, CO, $N_2$, $CF_4$, and $CO_2$, or by contacting an essentially inert gas, that is one with a reactivity comparable to nitrogen at a temperature of at least 2000° K. with a $C_1$ to $C_{10}$ compound containing fluorine and hydrogen in which the F to H ratio is greater than or equal to 1 and the fluorine to carbon ratio is greater than or equal to 1, preferably pentafluoroethane and/or trifluoromethane for a period of about 0.002 to 0.100 seconds. The reaction mixture is then cooled to a temperature below about 800° K. in less than about 1 second, preferably about 0.001 to 0.1 second and the tetrafluoroethylene recovered.

DETAILS OF THE INVENTION

This invention relates to a process for the preparation of tetrafluoroethylene, by heating in the presence of an essentially inert gas, i.e., one with a reactivity comparable to nitrogen, or Ar, HF, CO, $N_2$, $CF_4$ and $CO_2$, at a temperature of at least 2000° K. a $C_1$ to $C_{10}$ compound containing fluorine and hydrogen in which the F to H ratio is greater than or equal to 1 and the F to C ratio is greater than or equal to 1. The much preferred compounds are $CHF_3$ and $CF_3CHF_2$ with a heated, essentially inert gas, i.e., one with a reactivity comparable to $N_2$, or Ar, HF, CO, and $N_2$, $CF_4$, and $CO_2$. Much preferred is argon; the temperature utilized is greater than or equal to 2000° K.

The hot gas, preferably argon, is produced by passing the gas through a direct current (DC) arc or subjecting it to radio frequency energy. Much preferred is the DC arc. The argon gas may be passed through a plasma source, e.g., gun, and then allowed to relax (i.e. the state at which it may contain excited argon atoms but no free electrons) before coming in contact with the pentafluoroethane and/or trifluoromethane, for example.

The temperature of the argon gas is controlled by the power input to the plasma source. At an input of 4 kW, the argon gas in the reaction zone can achieve a temperature which is greater than or equal to 3000° K.

The contact time of the hot argon gas with the pentafluoroethane and/or trifluoromethane may range from about 0.002 to 0.100 second. The contact time is controlled by quenching the reaction via rapid cooling. The cooling is accomplished by rapid heat loss through the reactor walls or by injecting cold gas e.g., argon, into the reactor at a specified point.

The concentration of starting organic in the plasma gas can range from 0 to 100%. Preferred being about 0% in order to maintain a long electrode life.

The reaction may be run at virtually any pressure. preferred is 0.1 to 10 atmospheres, more preferred is 0.1 to 2.5 atmospheres and most preferred would be 0.1 atmospheres to atmospheric pressure.

Cooling may be performed as indicated above or by any means known to one skilled in the art. In general, the gaseous reaction product should be cooled to a temperature below about 800° K. in less than 1 second, preferably between about 0.001 and 0.1 second.

The reactor should be constructed of materials resistant to attack by the reactants or reaction products at the operating temperature. Preferred materials of this type include, for example, graphite, Inconel® alloy and Monel® alloy.

EXAMPLES

General Procedure

The reactor consists of a plasma source connected to a graphite tube 12" long with an ID of ½" to 1". The graphite tube is surrounded by a water cooled metal jacket. The distance between the graphite tube and the jacket is 0.0625". The graphite tube has three equally spaced inlets for introducing partially fluorinated hydrocarbon which are located 0.375" down from the top of the graphite tube. [The top of the graphite tube is that portion connected to the plasma source]. The tube also has three equally spaced inlets for introducing cold argon gas which are located 4.0" and 8.0" down from the top of the graphite tube.

Hot argon gas, produced by passing argon gas through the plasma source (electric arc), is introduced into one end of the graphite tube. Partially fluorinated hydrocarbon gas is then introduced into the reactor at high velocity. The reaction mixture is rapidly cooled via heat loss through the walls of the reactor as it passes through the tube or by introducing cold argon through the designated ports. A reaction sample is withdrawn by application of a vacuum to a water-cooled probe whose location may be varied downstream of the reactor in the cooling chamber. Between the pump and the probe is a device by means of which a sample vial (20 cc) may be inserted in line and filled with product gas. The vial is then removed and samples taken with hypodermic syringes for injection into a Hewlett Packard HP 5880 gas chromatograph. Flame-ionization detector analyzed gases were separated by a 15'×⅛" column containing 5% Krytox® perfluorinated polyether on 60/80 Carbopak BHT high surface area graphitized carbon hydrogen treated for deactivation. Thermal conductivity detector analyzed gases were separated by a 15'×⅛" column containing 80/100 Porapak® Q porous polymer of ethylvinylbenzene crosslinked with divinylbenzene.

EXAMPLES 1-3

The general procedure was followed using an Argon gas feed into the plasma source of 40 liters/minute. The graphite tube was 12"×½" ID. Pentafluoroethane was fed to the reactor at a rate of 1.68 liters/minute. The power Q supplied to the plasma source varied from 4 kW to 12 kW. The results are given in Table 1.

TABLE 1

Heating of $CF_3CHF_2$ with Hot Argon Gas to Produce $CF_2=CF_2$

| Product | 1 [4kW] | 2 [8kW] | 3 [12kW] |
|---|---|---|---|
| $CF_4$ | 2.3% | 14.3% | 27.1% |
| $CF_3CF_3$ | 10.6% | 6.4% | 3.1% |
| $CHF_3$ | 4.7% | 1.5% | 0.9% |
| $CF_2=CF_2$ | 51.5% | 75.8% | 66.9% |
| $CClF_3$ | 0.2% | 0.3% | 0.9% |
| $CF_3CF=CF_2$ | 2.6% | 1.7% | 1.1% |
| $CF_3CHF_2$ | 24.4% | 0.0% | 0.0% |

The reaction was run at atmospheric pressure. The lowest temperature was in all cases about 800° K. The reaction period in all cases has been estimated to be $\leq 0.01$ seconds. The cooling period is the rest of the time it takes the gas to pass through the tube or to come in contact with the quench gas and can readily be calculated by the data given in the examples, by one skilled in the art.

The yield of $CF_2=CF_2$ based on the conversion of $CF_3CHF_2$ was between 66.9 and 75.8%.

EXAMPLE 4

Example 3 was repeated with the exception that the reaction was quenched by the introduction of cold argon gas (80 liters/minute) at a point 8" down from the top of the graphite tube. The results are given in Table 2.

TABLE 2

| Product | 4 [12kW] |
|---|---|
| $CF_4$ | 23.1% |
| $CF_3CF_3$ | 3.4% |
| $CHF_3$ | 0.8% |
| $CF_2=CF_2$ | 71.1% |
| $CClF_3$ | 0.8% |
| $CF_3CF=CF_2$ | 0.9% |
| $CF_3CHF_2$ | 0.0% |

The reaction was run at atmospheric pressure. The lowest temperature was in all cases about 800° K. The reaction period in all cases has been estimated to be $\leq 0.01$ seconds. The cooling period is the rest of the time it takes the gas to pass through the tube or to come in contact with the quench gas and can readily be calculated by the data given in the examples, by one skilled in the art.

The results show that more rapid quenching with cold argon gas improves the yield of $CF_2=CF_2$.

EXAMPLES 5-6

For Example 5, Example 2 was repeated with the exception that trifluoromethane was fed to the reactor at a rate of 3 liters/minute in place of the pentafluoroethane. For Example 6, Example 5 was repeated with the exception that the reaction was quenched by the introduction of cold argon gas (40 liters/minute) at a point 4" down from the top of the graphite tube. The results are given in Table 3.

TABLE 3

Heating of $CHF_3$ with Hot Argon Gas to Produce $CF_2=CF_2$

| Product | 5 [8kW] | 6 [8kW] |
|---|---|---|
| $CF_4$ | 15% | 9% |
| $CF_3CF_3$ | 4% | 4% |
| $CHF_3$ | 7% | 5% |
| $CF_2=CF_2$ | 70% | 79% |
| $CF_3CF=CF_2$ | 4% | 3% |

The reaction was run at atmospheric pressure. The lowest temperature was in all cases about 800° K. The reaction period in all cases has been estimated to be $\leq 0.01$ seconds. The cooling period is the rest of the time it takes the gas to pass through the tube or to come in contact with the quench gas and can readily be calculated by the data given in the examples, by one skilled in the art.

The results show that more rapid quenching with cold argon gas improves the yield of $CF_2=CF_2$.

EXAMPLE 7

Heating of $CHF_3$ with Hot Argon Gas to Produce $CF_2=CF_2$ (TFE)

The general procedure was followed using an argon gas feed into the plasma source of 40 L/min. The graphite tube was 12"×½" ID. Trifluoromethane (HFC-23) was fed to the reactor at 3 L/min. The power supplied to the plasma source varied from 3 kW to 12 kW. The reaction was quenched by the introduction of cold argon gas (40 L/min.) at a point 4" down from the top of the graphite tube. The results are given in Table 1. HF is not included because it is scrubbed out using a 10% KOH solution prior to analysis.

TABLE 1

Heating of HFC-23 with Hot Argon Gas To Produce TFE

| Product (mol %) | % Power | | | | | | |
|---|---|---|---|---|---|---|---|
| | 20 | 30 | 40 | 50 | 60 | 70 | 80 |
| $CF_4$ | 1 | 5 | 10 | 11 | 12 | 12 | 13 |
| $CF_3CF_3$ | 3 | 6 | 4 | 5 | 4 | 4 | 5 |
| $CHF_3$ | 49 | 14 | 3 | 2 | 1 | 1 | 1 |
| $CF_2=CF_2$ | 47 | 72 | 82 | 80 | 82 | 82 | 80 |
| $CF_3CF=CF_2$ | 1 | 3 | 2 | 2 | 1 | 1 | 1 |

EXAMPLE 8

Heating of $CHF_3$ with Hot Argon Gas to Produce $CF_2=CF_2$ (TFE)

The reactants and procedure were identical to Example 1, except that in this case no quench was used.

TABLE 2

Heating of HFC-23 with Hot Argon Gas to Produce TFE

| Product (mol %) | % Power | | | | | | |
|---|---|---|---|---|---|---|---|
| | 20 | 30 | 40 | 50 | 60 | 70 | 80 |
| $CF_4$ | 1 | 5 | 14 | 25 | 35 | 43 | 33 |
| $CF_3CF_3$ | 3 | 10 | 15 | 14 | 10 | 6 | 2 |
| $CHF_3$ | 51 | 15 | 5 | 5 | 4 | 2 | 2 |
| $CF_2=CF_2$ | 43 | 63 | 61 | 53 | 47 | 47 | 63 |
| $CF_3CF=CF_2$ | 2 | 7 | 4 | 4 | 4 | 2 | 1 |

These results show the improved yields obtained when the reaction products are quenched more rapidly with cold argon gas.

I claim:

1. A process for the preparation of tetrafluoroethylene, by heating in the presence of an essentially inert gas, at a temperature of at least about 2000° K. a $C_2$ to $C_{10}$ compound containing fluorine and hydrogen in which the F to H ratio is greater than or equal to 1 and F to C ratio is greater than or equal to 1.

2. The process of claim 1 wherein the gas is selected from HF, Argon, CO, $CF_4$, and $CO_2$.

3. The process of claim 2 wherein the compound is $CF_3CHF_2$.

4. The process of claim 3 wherein the gas is argon.

5. The process of claim 4 wherein the argon is heated by passing through a DC arc.

6. The process of claim 3 wherein the gas is HF.

7. The process of claim 6 wherein the pressure is between 0.1 and 2 atmospheres.

8. The process of claim 7 wherein the pressure is atmospheric.

9. The process of claim 8 wherein after heating the compound is cooled to less than about 800° K.

* * * * *